US008101195B2

(12) United States Patent
Watanabe et al.

(10) Patent No.: US 8,101,195 B2
(45) Date of Patent: Jan. 24, 2012

(54) ARTIFICIAL LYMPH NODE FOR TREATING CANCER

(75) Inventors: Takeshi Watanabe, Yokohama (JP); Kouji Tanaka, Yokohama (JP)

(73) Assignee: RIKEN, Wako-shi (JP)

( * ) Notice: Subject to any disclaimer, the term of this patent is extended or adjusted under 35 U.S.C. 154(b) by 551 days.

(21) Appl. No.: 11/939,885

(22) Filed: Nov. 14, 2007

(65) Prior Publication Data

US 2009/0263428 A1 Oct. 22, 2009

(30) Foreign Application Priority Data

Dec. 7, 2006 (JP) ................................ 2006-331114

(51) Int. Cl.
*A61K 39/00* (2006.01)
*C12N 5/00* (2006.01)
*C12N 5/077* (2010.01)
*C12N 5/0784* (2010.01)
*C12N 5/10* (2006.01)

(52) U.S. Cl. .................................... 424/277.1; 435/325

(58) Field of Classification Search ........................ None
See application file for complete search history.

(56) References Cited

U.S. PATENT DOCUMENTS

| | | | | |
|---|---|---|---|---|
| 7,311,922 | B1 * | 12/2007 | Skeiky et al. | 424/248.1 |
| 2004/0097719 | A1 * | 5/2004 | Agrawal et al. | 536/23.2 |

FOREIGN PATENT DOCUMENTS

| | | | |
|---|---|---|---|
| JP | 2006-129839 A | | 5/2006 |
| WO | WO03/100034 | * | 12/2003 |

OTHER PUBLICATIONS

Dillman et al (Cancer Biotherapy and Radiopharmaceuticals, 2004, vol. 19, pp. 658-665).*
Seliger (Biodrugs, 2005, vol. 19, pp. 347-354).*
Abstract of Hernberg (Medical Oncology, 1999, vol. 16, pp. 145-153).*
Jeong et al (Journal of Biotechnology, 2002, vol. 94, pp. 255-263).*
Salem et al (Journal of Immunotherapy, May/Jun. 2005, vol. 28, pp. 220-228).*
Thompson et al (Journal of Leukocyte Biology, Dec. 2005, vol. 78, pp. 1273-1280).*
Suematsu et al., *Nature Biotechnology*, 22(12): 1539-1545 (Dec. 2004).
Okamoto et al., *J. Clin. Invest.*, 117: 997-1007 (2007).

* cited by examiner

*Primary Examiner* — Karen Canella
(74) *Attorney, Agent, or Firm* — Leydig, Voit & Mayer, Ltd.

(57) ABSTRACT

Provided is an artificial lymph node that is persistently effective in cancer treatment in vivo.
A method of producing an artificial lymph node capable of inducing cancer antigen-specific immune responses, comprising the following steps: (a) a step for immunizing a non-human animal using a cancer antigen and an adjuvant capable of inducing cellular immunity; and (b) a step for transplanting an artificial lymph node material consisting of a polymeric biomaterial comprising cytokine-producing stromal cells and dendritic cells to the immunized non-human animal, an artificial lymph node capable of inducing cancer antigen-specific immune responses obtained by the method of production, a cancer therapeutic agent comprising the artificial lymph node, and a kit for producing an artificial lymph node for cancer treatment comprising the following: (a) a cancer antigen; (b) an adjuvant capable of inducing cellular immunity; (c) a cytokine expression vector and stromal cells, or stromal cells incorporating a cytokine expression vector; (d) dendritic cells; and (e) a polymeric biomaterial.

21 Claims, 5 Drawing Sheets

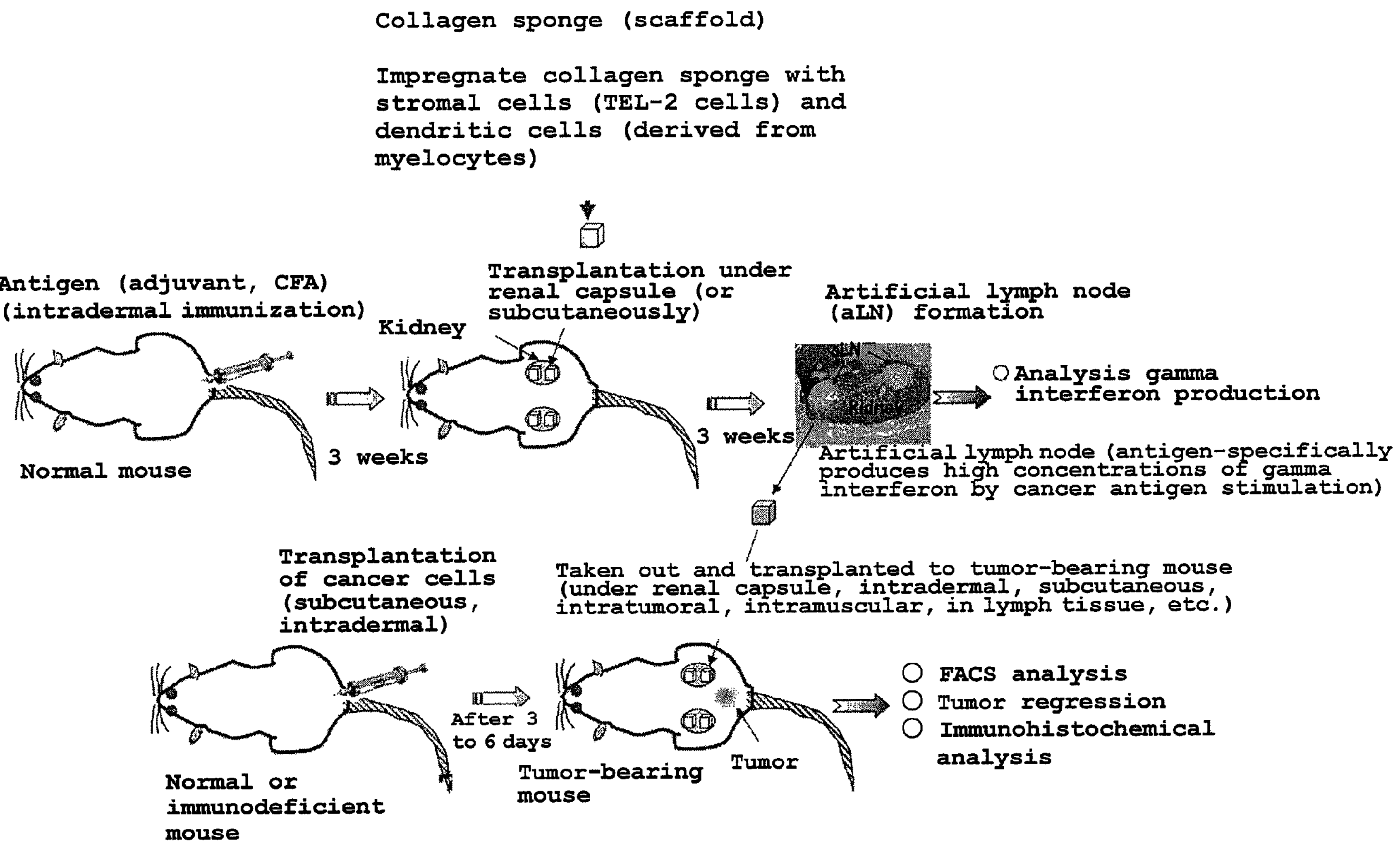
FIG. 1
Collagen sponge (scaffold)
Impregnate collagen sponge with stromal cells (TEL-2 cells) and dendritic cells (derived from myelocytes)
Antigen (adjuvant, CFA) (intradermal immunization)
Kidney
Transplantation under renal capsule (or subcutaneously)
Artificial lymph node (aLN) formation
Analysis gamma interferon production
Normal mouse
3 weeks
3 weeks
Artificial lymph node (antigen-specifically produces high concentrations of gamma interferon by cancer antigen stimulation)
Transplantation of cancer cells (subcutaneous, intradermal)
Taken out and transplanted to tumor-bearing mouse (under renal capsule, intradermal, subcutaneous, intratumoral, intramuscular, in lymph tissue, etc.)
FACS analysis
Tumor regression
Immunohistochemical analysis
After 3 to 6 days
Normal or immunodeficient mouse
Tumor-bearing mouse
Tumor FIG. 3
A
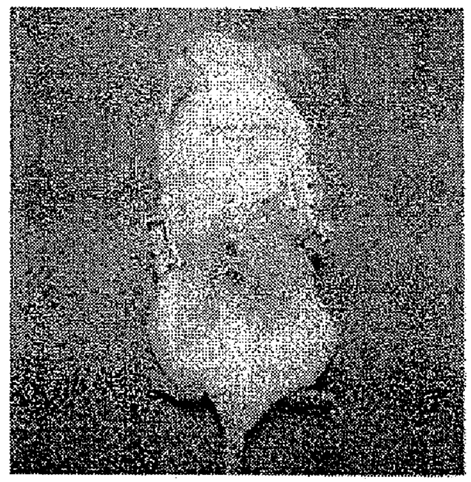
B
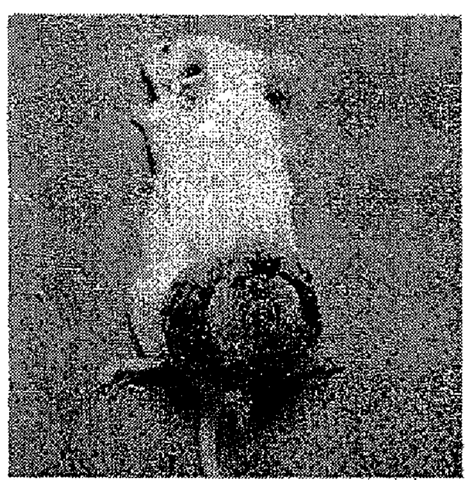
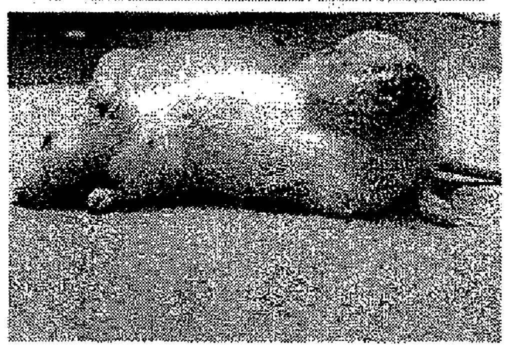
aLN-transplanted
Not-transplanted FIG. 5
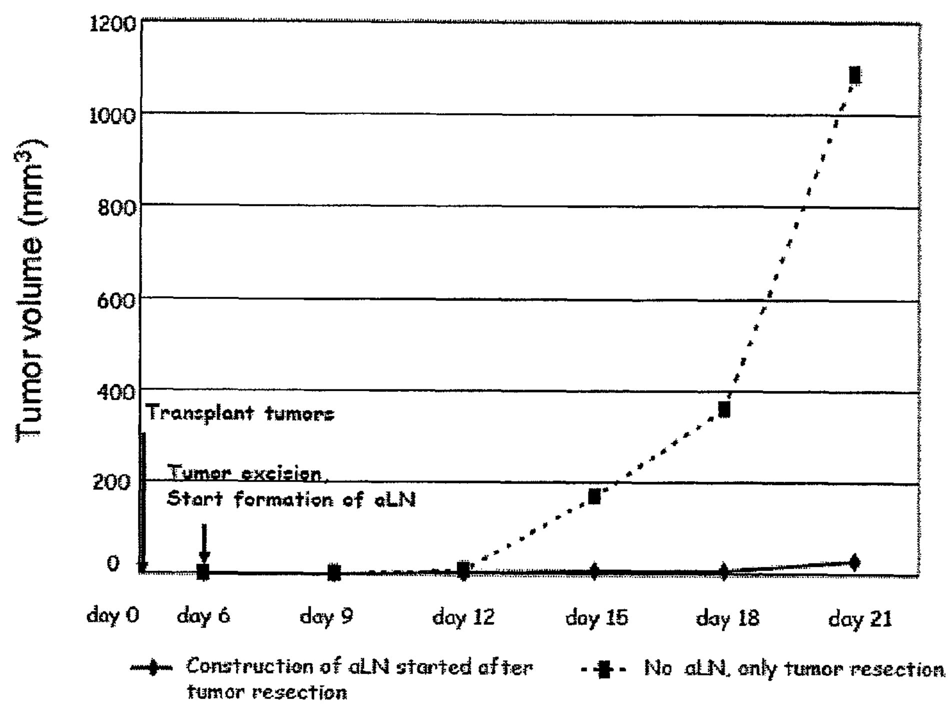
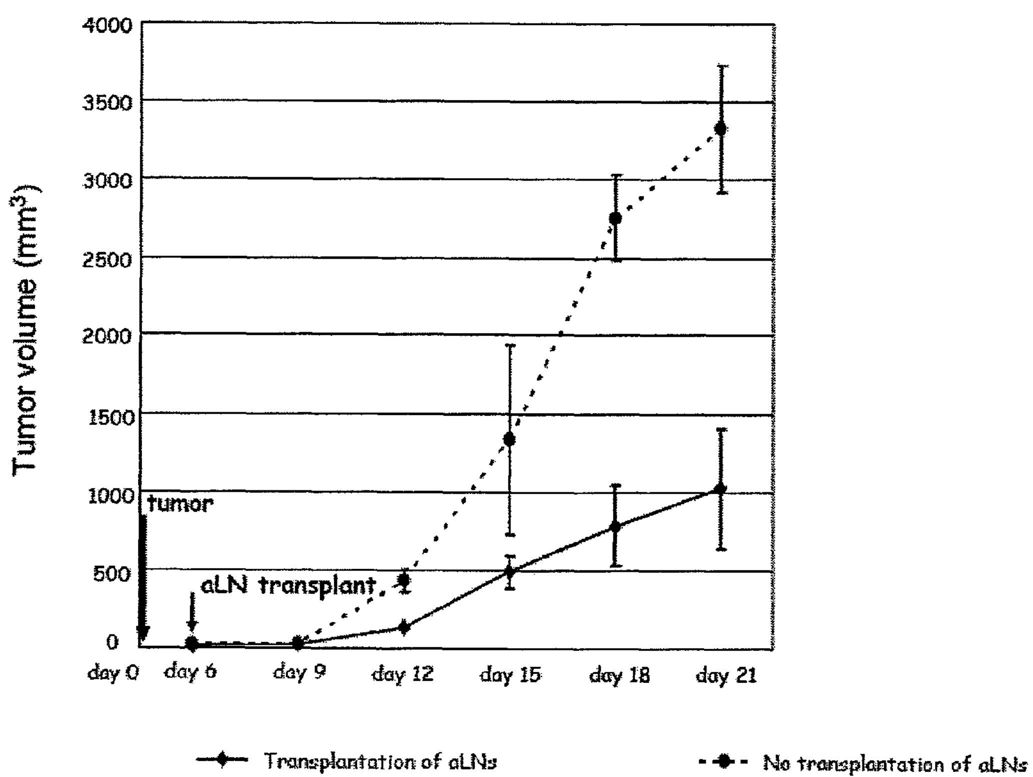

ARTIFICIAL LYMPH NODE FOR TREATING CANCER

TECHNICAL FIELD

The present invention relates to an artificial lymph node for cancer treatment. More specifically, the present invention relates to a method of supplying T cells that produce interferon γ in a cancer antigen specific manner.

BACKGROUND ART

The lymph node is a site where it allows lymphocytes to interact with antigens and antigen-presenting cells to initiate antigen-specific immune responses (adaptive immunity) by assuming a highly organized three-dimensional structure, and is an essential organ for body defense.

The present inventors demonstrated that on the assumption of stromal cells, a cytokine and a polymeric biomaterial as the three essential components for the construction of an artificial lymph tissue, by incorporating stromal cells and a cytokine to a three-dimensional structure configured with a polymeric biomaterial, and transplanting this assembly under the renal capsule of a mouse, a tissue structurally similar to secondary lymph tissue (artificial lymph node) can be constructed 3 weeks after transplantation, and that by adding bone marrow-derived activated dendritic cells to this combination of the three components, the efficiency of artificial lymph node construction can be improved (about 60 to 80% of transplanted tissue) (see JP-A-2004-255110 and Sachiko Suematsu and Takeshi Watanabe, Nature Biotechnology vol. 22, 1539-1545, 2004). The present inventors also succeeded in providing an artificial lymph node that produces an antigen-specific antibody capable of inducing efficient adaptive immune responses in immunodeficient individuals (JP-A-2006-129839). These artificial lymph nodes exhibit functions equivalent to those of innate lymph nodes in vivo. The artificial lymph node described in JP-A-2004-255110 is characterized in that a T cell region and a B cell region are present with distinct separation as in ordinary lymph nodes, and that regarding the ratio of CD4T cells and CD8T cells in the artificial lymph node, CD4T cells account for the majority, this ratio being similar to the ratio of CD4T cells and CD8T cells in the T cell region of normal lymph nodes. The artificial lymph node described in JP-A-2006-129839 is characterized in that along with T cells and B cells, dendritic cells, which play an important role in immune responses, are present, that a B cell region comprising a network of follicular dendritic cells is present in the central portion thereof, that germinal center B cell-like B cells are present, that plasma cells which are antibody-producing cells are present, and the like.

Meanwhile, various immunotherapies have been attempted in cancer treatment; for example, vaccination using a cancer peptide antigen, vaccination using a cancer protein antigen, various cellular therapies using IL-2 activated lymphocytes, NKT cells, dendritic cells and the like, cytokine therapy, antibody preparations, BRM non-specific immunotherapy using cell body components of BCG or tubercle bacillus and the like, and the like are known, but to obtain persistent immunostimulatory effects in vivo, these therapies need to be applied a plurality of times.

DISCLOSURE OF THE INVENTION

It is an object of the present invention to provide an artificial lymph node that is persistently effective in cancer treatment in vivo.

The present inventors diligently investigated to solve the above-described problems and, as a result, succeeded in constructing a therapeutic artificial lymph node of cancer antigen-specific CD8-positive killer T cells by using an animal immunized with a cancer antigen and a particular adjuvant in combination, and completed the present invention.

Accordingly, the present invention provides the following:

[1] A method of producing an artificial lymph node capable of inducing cancer antigen-specific immune responses, comprising the following steps:

(a) a step for immunizing a non-human animal using a cancer antigen and an adjuvant capable of inducing cellular immunity; and (b) a step for transplanting an artificial lymph node material consisting of a polymeric biomaterial comprising cytokine-producing stromal cells and dendritic cells to the immunized non-human animal.

[2] The method of production described in [1] above, further comprising the following step:

(c) a step for recovering the artificial lymph node constructed in the foregoing transplantation step from the recipient non-human animal.

[3] The method of production described in [1] above, wherein the adjuvant is at least one kind selected from the group consisting of Freund's complete adjuvant, CpG adjuvant, liposome, BCG, polyI:C, R848, lipopolysaccharide and aluminum hydroxide.

[4] The method of production described in [1] above, wherein the dendritic cells are myeloid cell-derived dendritic cells.

[5] The method of production described in [1] above, wherein the polymeric biomaterial is collagen sponge.

[6] The method of production described in [1] above, wherein the cytokine is a lymphotoxin and/or a chemokine.

[7] The method of production described in [1] above, wherein the non-human animal is a non-human mammal.

[8] An artificial lymph node capable of inducing cancer antigen-specific immune responses, obtained by the method of production described in [1] above.

[9] An artificial lymph node capable of inducing cancer antigen-specific immune responses, obtained by the method of production described in [2] above.

[10] The artificial lymph node described in [8] above, which prevalently comprises cancer antigen-specific interferon γ-producing cells when stimulated with the cancer antigen used in the immunization step in [1] above.

[11] The artificial lymph node described in [9] above, which prevalently comprises cancer antigen-specific interferon γ-producing cells when stimulated with the cancer antigen used in the immunization step in [1] above.

[12] A cancer therapeutic agent comprising the artificial lymph node described in [8] above.

[13] A cancer therapeutic agent comprising the artificial lymph node described in [9] above.

[14] A kit for producing an artificial lymph node for cancer treatment, comprising the following:

(a) a cancer antigen;

(b) an adjuvant capable of inducing cellular immunity;

(c) a cytokine expression vector and stromal cells, or stromal cells incorporating a cytokine expression vector;

(d) dendritic cells; and (e) a polymeric biomaterial.

[15] The kit described in [14] above, wherein the adjuvant is at least one kind selected from the group consisting of Freund's complete adjuvant, CpG adjuvant, liposome, BCG, polyI:C, R848, lipopolysaccharide and aluminum hydroxide.

[16] The kit described in [14] above, wherein the dendritic cells are myeloid cell-derived dendritic cells.

[17] The kit described in [14] above, wherein the polymeric biomaterial is collagen sponge.

[18] The kit described in [14] above, wherein the cytokine is a lymphotoxin and/or a chemokine.

[19] A method of producing an artificial lymph node capable of inducing cancer antigen-specific immune responses, comprising the following steps:

(a1) a step for immunizing an animal using an cancer antigen and an adjuvant capable of inducing cellular immunity; and (b1) a step for transplanting an artificial lymph node material consisting of a polymeric biomaterial comprising cytokine-producing stromal cells and dendritic cells to the immunized animal.

[20] The method of production described in [19] above, wherein the foregoing immunization step is performed with cancer cells born in the body of the animal.

[21] The method of production described in [19] above, wherein the animal is a human.

[22] The method of production described in [19] above, wherein the foregoing transplantation step is performed before, during, or after surgery for a cancer in the animal.

[23] An antigen-specific therapeutic method for a cancer, comprising the following steps:

(a1) a step for immunizing an animal using a cancer antigen and an adjuvant capable of inducing cellular immunity; and (b1) a step for transplanting an artificial lymph node material consisting of a polymeric biomaterial comprising cytokine-producing stromal cells and dendritic cells to the immunized animal.

[24] The therapeutic method described in [23] above, wherein the foregoing immunization step is performed with cancer cells born in the body of the animal.

[25] The therapeutic method described in [23] above, wherein the animal is a human.

According to the method and kit of the present invention for producing an artificial lymph node, an artificial lymph node capable of inducing cancer antigen-specific immune responses can be provided in a tailor-made manner. The artificial lymph node of the present invention surpasses innate lymph nodes in terms of interferon γ productivity in response to cancer antigen stimulation, and as a source of cytotoxic T cells (CD8-positive killer T cells), and is useful in the treatment of cancer. According to the therapeutic agent of cancer of the present invention, by comprising the aforementioned artificial lymph node, interferon γ productivity in vivo is increased, and interferon γ production persists effectively, compared with conventional cancer immunotherapy; therefore, a cancer therapeutic effect is expected with less burden on the patients. Furthermore, the artificial lymph node of the present invention is also capable of concentrating immune cells having cancer cytotoxic activity, such as NK cells and NKT cells, and is expected to be also therapeutically effective against cancer cells with decreased expression of MHC.

BRIEF DESCRIPTION OF THE DRAWINGS

FIG. 1 shows a schematic diagram of the step for producing an artificial lymph node in a Production Example.

FIG. 2A shows interferon γ production in an artificial lymph node; FIG. 2B shows that the interferon γ-producing cells are CD8-positive cells, CD4-positive cells and NK cells. FIG. 2C shows that CD8-positive killer cells derived from an artificial lymph node can grow in the spleen and produce interferon γ; FIG. 2D shows that no interferon γ is produced without transplantation of an artificial lymph node.

FIG. 3 shows photographs showing a cancer regression effect in a cancer-bearing mouse with a transplanted artificial lymph node. FIG. 3A is a panel for a mouse with a transplanted artificial lymph node; FIG. 3B is a panel for a mouse without transplantation.

FIG. 5 shows graphs showing the suppressive effects of an artificial lymph node on cancer recurrences or primary cancers. The upper panel in FIG. 5 is a graph of an examination of recurrences after cancer resection. The lower panel in FIG. 5 is a graph of an examination of the effects of a transplanted artificial lymph node on primary cancers.

BEST MODE FOR CARRYING OUT THE INVENTION

Figure 2:
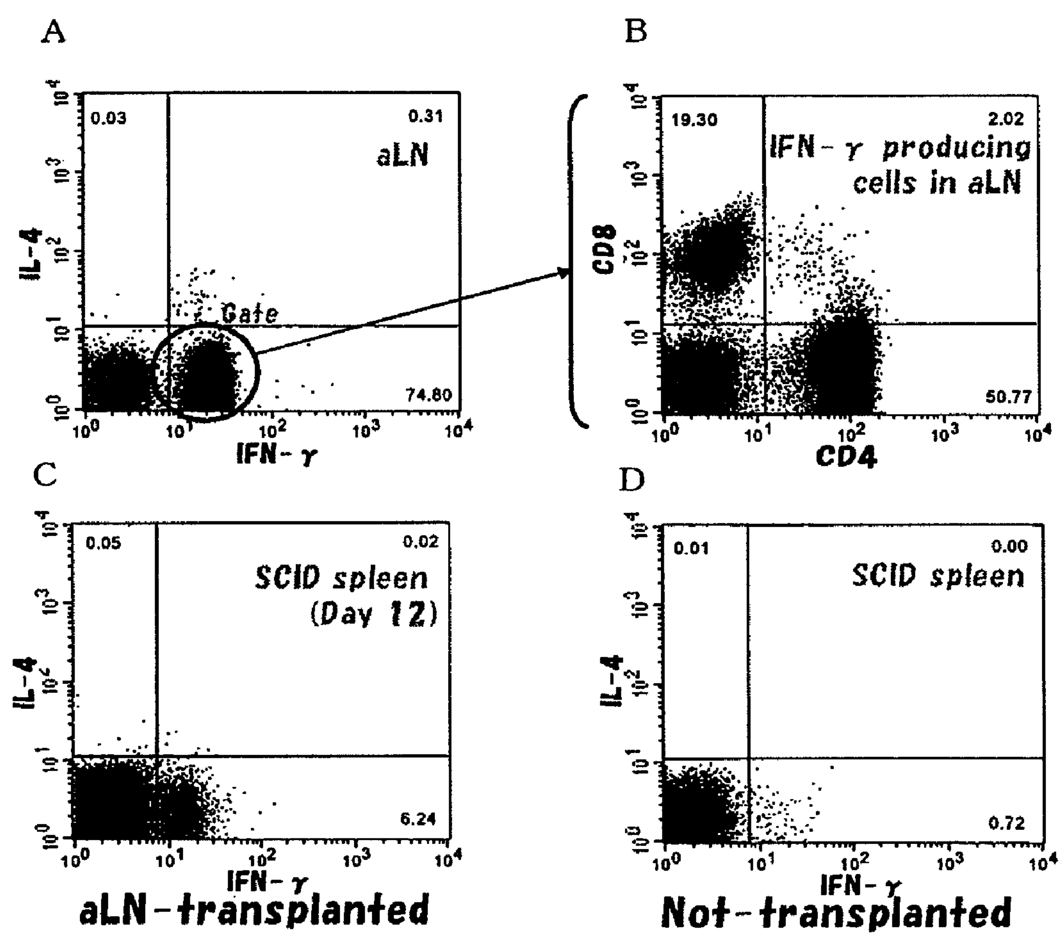
FIG. 2 is a graph showing the results of an examination of interferon γ production after stimulation of an artificial lymph node with a cancer antigen.

The present invention provides a method of producing an artificial lymph node capable of inducing cancer antigen-specific immune responses, which method comprises the following steps:

(a) a step for immunizing a non-human animal using a cancer antigen and an adjuvant capable of inducing cellular immunity; and (b) a step for transplanting an artificial lymph node material consisting of a polymeric biomaterial comprising cytokine-producing stromal cells and dendritic cells to the immunized non-human animal.

Preferably, the production method of the present invention further comprises the following step:

(c) a step for recovering the artificial lymph node constructed in the foregoing transplantation step from the recipient non-human animal.

The present invention also provides an artificial lymph node capable of inducing cancer antigen-specific immune responses (hereinafter abbreviated “cancer antigen-specific artificial lymph node”), comprising cytokine-producing stromal cells, dendritic cells and a polymeric biomaterial, obtained by the above-described production method.

The lymph node is a lymphoid tissue (a tissue wherein lymphocytes interact with non-lymphoid cells) that plays an important role in maturation and adaptive immune responses of lymphoid cells. Lymphoid tissues can be classified into primary lymph tissues and secondary lymph tissues. Primary lymph tissues are places of lymphocyte production, and the bone marrow and the thymus are included therein. Secondary lymph tissues have a special structure for capturing antigens, and serve as places where adaptive immune responses are initiated. Secondary lymph tissues (also referred to as peripheral lymph tissues) include the spleen, lymph nodes, mucosa-related lymphatic tissues (tonsil, trachea-related lymphatic tissue, gut-related lymphatic tissue, Peyer’s patches (PP), aggregates of other lymphoid cells).

In the present invention, cancer antigens refer to protein components that are expressed in excess in cancer cells and attacked by immune cells, and include currently known cancer antigens and cancer antigens that will be discovered in the future. As used in the present invention, the aforementioned cancer antigens are preferably in the form of cancer antigen peptides that are degraded in the cytoplasm of cancer cells and presented to cancer cell surfaces along with a class I MHC molecule (class I HLA molecule in the case of humans). Cancer antigens are also capable of simultaneously activating cancer antigen-specific helper T cells; it is necessary to promote the activation and growth of killer T cells in order to obtain a more effective antitumor effect. Therefore, cancer antigen peptides that are presented to T cells along with a class II MHC molecule (in case of humans, class II HLA molecule) by dendritic cells are also included in cancer antigens. In one embodiment of the present invention, the cancer antigen may be cancer cells per se.

As specific examples of the cancer antigen, CEA, MAGE-1, MAGE-2, MAGE-3, HER2/neu, MART-1, MUC-1, PR-1, G250, NY-ESO-1, p53, PM17, PSA-1, PSCA, Proteinase 3, Survivin, Survivin 2B, hTERT, Gp-100, Tyrosinase, Livin 7, WT1 and the like are known, but these are not to be construed as limiting. As the cancer antigen peptide, all peptides that can be selected from among the aforementioned cancer antigens can be mentioned. The length of the cancer antigen peptide is normally 7 to 12 amino acids, preferably 8 to 10 amino acids. Regarding the sequence of the cancer antigen peptide, those skilled in the art can estimate its amino acid sequence using an HLA-binding peptide prediction program and the like, and it is also possible to isolate the cancer antigen peptide being presented by the cancer cells of the subject of treatment to the cell surfaces by a conventional method, and to determine the amino acid sequence thereof. For the purpose of effective treatment of cancer, it is preferable to identify the type of MHC (HLA) of the subject of treatment, to examine for the presence or absence of cancer antigen overexpression, and to select a cancer antigen comprising the cancer antigen peptide. In one embodiment of the present invention, specific examples of the cancer antigen may be cancer cells per se that can be predicted to have the aforementioned cancer antigen peptide presented thereto.

The cancer antigen-specific artificial lymph node of the present invention is capable of supplying interferon γ-producing cells that react specifically with cancer cells in a subject wherein the cancer antigen is expressed. As mentioned herein, interferon γ-producing cells refer to CD8-positive cells, CD4-positive cells, NK cells, NKT cells and the like. Described below is a method of producing such an artificial lymph node.

(a) A step for immunizing a non-human animal using a cancer antigen and an adjuvant capable of inducing cellular immunity The non-human animal to be immunized with a cancer antigen is preferably a non-human mammal (for example, monkeys, horses, bovines, goat, sheep, pigs, dogs, cats, rabbits, guinea pigs, hamsters, rats, mice and the like).

These animals are immunized with one of the aforementioned cancer antigens selected according to the purpose of treatment and the like before transplantation of a polymeric biomaterial (hereinafter, also referred to as primary immunization). By this primary immunization, the immunocompetent cells in the secondary lymph tissue and the like of the animal are antigen-stimulated, and antigen-specific T cells are produced.

In the immunization, the cancer antigen is administered to the animal along with an adjuvant capable of inducing cellular immunity. As the adjuvant, Freund's complete adjuvant, the CpG adjuvant, liposome, BCG, polyI:C, R848 (resiquimod: 4-amino-2-ethoxymethyl-α,α-dimethyl-1H-imidazo[4,5-c]quinolin-1-ethanol), lipopolysaccharide (LPS), aluminum hydroxide (Alum), R837 (imiquimod: 1-(2-methylpropyl)-1H-imidazo[4,5-c]quinolin-4-amine), loxoribine (7-allyl-8-oxoguanosine), bropirimine (2-amino-5-bromo-6-phenyl-4-pyrimidinone) and the like can be mentioned. In the present invention, it is preferable to use at least one kind selected from the group consisting of Freund's complete adjuvant, the CpG adjuvant, liposome, BCG, polyI:C, R848, lipopolysaccharide (LPS) and aluminum hydroxide (Alum), and more preferably Freund's complete adjuvant or the CpG adjuvant is used.

The amount of cancer antigen used for primary immunization varies depending on the kind, age, and body weight of the animal used, route of administration and the like. In the present invention, the route of administration is preferably intradermal. For example, in the case of intradermal administration to an adult mouse, an amount of antigen of 10 μg to 1000 μg, preferably 10 to 100 μg, can be mentioned. The amount of adjuvant used for primary immunization varies depending on the kind of adjuvant, the kind, age, and body weight of the animal used, route of administration and the like, and can be determined as appropriate by those skilled in the art.

Furthermore, in order to secure antigen stimulation of immunocompetent cells, primary immunization may be repeated one or several times (for example, 1 to 3 times) at intervals of 1 to 2 weeks. If primary immunization is repeated, the antigen can preferably be administered intravenously (i.v.). However, in a cancer-bearing living organism, immunization is established with antigen stimulation by the cancer antigen molecule circulating in the blood of the organism receiving an artificial lymph node.

(b) A step for transplanting an artificial lymph node material consisting of a polymeric biomaterial comprising cytokine-producing stromal cells and dendritic cells to the immunized non-human animal In this step, an artificial lymph node material is transplanted to the aforementioned non-human animal. The artificial lymph node material consists of a polymeric biomaterial comprising cytokine-producing stromal cells and dendritic cells. Described below are the components of the artificial lymph node material.

(Cytokines)

Cytokines generically mean proteinous bioactive substances that control the growth and differentiation of various blood cells, and sometimes also refer to growth factors and growth suppressive factors for cells, including non-immune system cells. Cytokines are classified by action characteristics into interleukins, colony-stimulating factors, interferons, chemokines, lymphokines, tumor necrosis factors (TNFs) and the like. The interleukin used in the present invention is not particularly limited, and can be optionally chosen from among IL-1 to IL-18. As examples of the colony-stimulating factors, G-CSF, M-CSF, GM-CSF and the like can be used. As examples of the interferons (IFNs), IFN-α, IFN-β, IFN-γ and the like can be used. As examples of the chemokines, CCL21 (also referred to as SLC (secondary lymphoid tissue chemokine)), CXCL13 (also referred to as BLC (B lymphocyte chemoattractant)), CCL19 (also referred to as ELC (Epstein-Barr virus-induced molecule 1 ligand chemokine)) and the like can be used. As examples of the TNFs, TNF-α, TNF-β and the like can be used. TNF-β is also referred to as lymphotoxin α (LTα). LTα is the first molecule to have been found to be essential for the organogenesis of the lymph node (LN) and Peyer's patches (PP), and for the formation of the normal spleen tissue structure. In addition to LTα, LTβ exists as a lymphotoxin. These lymphotoxins can also be used in the present invention.

The cytokine used in the present invention is preferably a lymphotoxin and/or a chemokine, more preferably LTα, CCL21, CXCL13, and/or CCL19.

These cytokines are commercially available, and can easily be obtained.

(Stromal Cells)

Stromal cells generically refer to cells that constitute microenvironments surrounding various cells having gland- or organ-specific proper functions (parenchymal cells), and are also referred to as "parenchyma support cells". As such, "parenchyma support cells" literally physically support the cells of parenchyma, and are thought to also exhibit a supportive function for exerting some effect on the partner cells by mutual interactions. Stromal cells are also referred to as "supportive cells" or "interstitial cells".

As examples of the stromal cells used in the present invention, TEL-2 stromal cells, which have been established from the thymus of a 2-week-old BALB/c mouse (Eur. J. Immunol 20: 47-53, 1990), can be mentioned. These TEL-2 stromal cells can be maintained and passaged by cultivation using an RPMI-1640 medium supplemented with 10% inactivated FCS and 50 μM 2-mercaptoethanol. For example, cells in culture may be harvested from a culture dish by means of a Trypsin-EDTA solution and subcultured in 1/10 to 1/20 dilutions every 3 days.

(Cytokine-Producing Stromal Cells)

The cytokine-producing stromal cells used in the present invention can be prepared by constructing an expression vector comprising a cytokine-encoding gene (also referred to as cytokine expression vector), and introducing this expression vector into stromal cells by a commonly known transfection technology. Genetic information on various cytokines is publicly known, and can be obtained from, for example, publicly accessible genetic databases such as GenBank.

For example, to allow TEL-2 stromal cells to produce one of the above-described cytokines or chemokines, an expression vector comprising the gene that encodes the cytokine or chemokine and a drug resistance gene (for example, neomycin resistance gene) is introduced by lipofection and the like, and the cells are cultured using a selection medium supplemented with a drug (for example, G418 (500 μg/ml)) for 10 days to 2 weeks, whereby a drug resistant cell line can be obtained. The expression of the introduced gene can be confirmed by measuring the biological activity of the cell culture supernatant. For biological activity determinations, in the case of a chemokine, for example, a chemotaxis assay for measuring the migratory activity of T cells or B cells can be used.

(Polymeric Biomaterial)

As the polymeric biomaterial used in the present invention, a biocompatible polymer material having a three-dimensional structural backbone can be used. In the present invention, "a three-dimensional structural backbone" means "a scaffold for allowing stromal cells and lymph node component cells such as lymphocytes and dendritic cells to organize themselves three-dimensionally". "A biocompatible polymer material" means "a material composed of various polymers to minimize the reactions by a living organism to eliminate the material as a foreign substance when applied to the living organism by a certain method".

As examples of such a polymeric biomaterial, collagen, glycosaminoglycan, polyglycolic acid, poly-L-lactic acid and the like can be mentioned. Non-biodegradable materials such as nylon, polyester, polyurethane and ethylene vinyl acetate can also be used singly or in combination.

Collagen sponge is a component of the living body, and is preferable as the polymeric biomaterial in view of reduced inflammatory reactions and immune responses. "Collagen sponge" means a porous material having a sponge structure comprising collagen; for example, collagen for three-dimensional tissue culture prepared by freeze-drying bovine Achilles tendon insoluble collagen to obtain a porous sponge and the like can be utilized in the present invention.

The polymeric biomaterial used in the present invention may be biodegradable or non-biodegradable; any optionally chosen material can be used, as long as it is unlikely to cause immune responses due to the antigenicity thereof and/or inflammatory reactions due to physical stimulation when transplanted to a living organism. However, in order to organize stromal cells and immunocompetent cells into a three-dimensional structure and to function as an artificial lymph node, a pore size suitable for the construction of the artificial lymph node or an overall size of the polymer material transplanted is chosen as appropriate in the case of, for example, a porous polymer material. The pore size and overall size of this graft can be determined as appropriate by those skilled in the art.

(Dendritic Cells)

Dendritic cells generically refer to a group of cells having a branch-shaped form derived from hematopoietic stem cells, and are widely distributed not only in the lymph system organs, but also in other organs. Dendritic cells present cancer antigens on the cell surfaces thereof, thus serving as an effective stimulant for promoting the activation and growth of killer T cells (CTL).

The dendritic cells used in the present invention can be obtained by culturing a progenitor thereof. Progenitors for dendritic cells originate from hematopoietic stem cells derived from the bone marrow, umbilical blood, or peripheral blood, monocytes derived from peripheral blood and the like. In the present invention, the dendritic cells are preferably those derived from myeloid cells because (1) they allow the pulsation of antigen peptides in vitro, and also because (2) they can contain bone marrow hematopoietic cell-derived inducer cells involved in lymph node formation. Dendritic cell progenitors can be separated and purified from a suspension of collected bone marrow fluid, umbilical blood, or peripheral blood and the like as required.

To allow a group of cells containing dendritic cell progenitors to grow and differentiate into mature/activated dendritic cells, an appropriate inducer is used. As the inducer, a selected cytokine can be used. As examples of the cytokine, GM-CSF, IL-1, IL-4, IFN-α, TNF-α and the like can be mentioned; these cytokines can be used singly or in appropriate combinations.

For example, dendritic cells can be matured/activated by culturing them using an RPMI-1640 medium or McCoy's medium supplemented with 5 to 20 ng/ml of one of the above-described cytokines, with an activation factor such as LPS (lipopolysaccharide) added to achieve final activation. Furthermore, with the addition of a cancer antigen (preferably, a cancer antigen selected according to the purpose of treatment and the like) along with this LPS, dendritic cells can be antigen-pulsated.

(Preparation of Artificial Lymph Node Material)

By allowing the aforementioned cytokine-producing stromal cells and dendritic cells (preferably, activated dendritic cells pulsated with a cancer antigen) to adhere to a polymeric biomaterial, an artificial lymph node material is prepared. To allow cytokine-producing stromal cells to adhere to a polymeric biomaterial, the polymeric biomaterial is immersed in a highly concentrated cell suspension, or these cells are injected to the polymeric biomaterial using a syringe equipped with an injection needle (for example, 26 gauge). To allow dendritic cells to adhere to a polymeric biomaterial, the polymeric biomaterial is immersed in a highly concentrated cell suspension, or these cells are injected to the polymeric biomaterial using an injection needle (for example, 26 gauge).

The artificial lymph node material thus prepared is transplanted to an animal tissue (for example, under the renal capsule, subcutaneous, intraperitoneal and the like), preferably after one week following primary immunization (the final immunization if primary immunization is performed a plurality of times).

In order to secure the induction of interferon γ-producing cells in such an artificial lymph node, several weeks (for example, 1 to 3 weeks) after transplantation of the artificial lymph node material to the animal undergoing primary immunization, secondary immunization may be performed with the same antigen as that used for primary immunization. Furthermore, in order to further secure the induction of interferon γ-producing cells, secondary immunization may be repeated several times (for example, 1 to 3 times) at intervals of 1 to 2 weeks. Secondary immunization can also be fully induced by a cancer antigen circulating in a cancer-bearing organism when the artificial lymph node is transplanted to the cancer-bearing organism.

The amount of antigen used for secondary immunization varies depending on the kind, age, and body weight of the animal used, route of administration and the like; for example, in the case of intradermal administration to an adult mouse, an amount of antigen of 10 μg to 1000 μg, preferably 10 to 100 μg, can be mentioned.

(c) A step for recovering the artificial lymph node constructed in the foregoing transplantation step from the recipient non-human animal.

About 3 weeks after transplantation of the aforementioned artificial lymph node material, the cancer antigen-specific artificial lymph node of the present invention can be constructed in the body of the animal. The cancer antigen-specific artificial lymph node thus constructed is recovered from the living organism, and then may be re-transplanted to another animal for secondary immunization, or for in vitro culture, or may be used for treating a cancer-bearing individual, or may be stored in a culture medium supplemented with an appropriate preservative (for example, 10% DMSO) at a low temperature under −80° C. and freshly prepared before use.

The subject of transplantation of the artificial lymph node thus constructed is a human or a non-human animal, and the non-human animal is preferably a non-human mammal (for example, monkeys, horses, bovines, goat, sheep, pigs, dogs, cats, rabbits, guinea pigs, hamsters, rats, mice and the like). In the case of transplantation to a human, to prevent graft rejection, it is preferable to use the humanized artificial lymph node described below.

In one embodiment, the present invention provides a humanized cancer antigen-specific artificial lymph node. The humanized cancer antigen-specific artificial lymph node can be constructed by, for example, introducing human lymphocytes, a human lymphocyte progenitor, myeloid cells, and/or hematopoietic stem cells and the like into an immunodeficient animal (for example, an immunodeficient mouse) to construct a human immune system in the body of the immunodeficient animal, thereafter primarily immunizing this animal having the human immune system with a cancer antigen selected according to the purpose of treatment and the like and an adjuvant in accordance with the above-described method, transplanting an artificial lymph node material consisting of a polymeric biomaterial having stromal cells and dendritic cells attached thereto, and, as required, secondarily immunizing the animal with the same antigen.

In another embodiment, the present invention provides a cancer antigen-specific artificial lymph node for human. The cancer antigen-specific artificial lymph node for human can be constructed by, for example, transplanting an artificial lymph node material consisting of a polymeric biomaterial having stromal cells and dendritic cells attached thereto, and retaining it in vivo for a predetermined time because primary immunization with a cancer antigen has been established in the body of a cancer patient. In the present invention, by transplanting a part of the artificial lymph node material of the present invention directly to a cancer patient to be treated, cancer can be treated. The present invention also provides such a method of cancer treatment.

(Cultivation of Artificial Lymph Node)

For culturing the cancer antigen-specific artificial lymph node of the present invention in vitro, the artificial lymph node recovered from a living organism is cultured after being transferred to a culture medium supplemented with cytokines and other stimulating factors for the continued survival and growth of lymphocytes and dendritic cells. A sustained-release material may be added to this culture system. When the cancer antigen-specific artificial lymph node is cultured in vitro, cultivation is continued while supplementing the culture system with a fresh supply of hematopoietic stem cells, lymphocyte or dendritic cell progenitors, and lymphocytes, dendritic cells and the like.

The cancer antigen-specific artificial lymph node of the present invention is capable of inducing cancer antigen-specific immune responses. As shown in an Example, when a cancer antigen admixed with an adjuvant (Freund's complete adjuvant) is injected intradermally to an animal (mouse) receiving an artificial lymph node material transplanted, interferon γ-producing T cells are induced in the artificial lymph node at a very high frequency (about 75%). It was shown that when this artificial lymph node was further transplanted to a cancer-bearing animal (cancer-bearing nude mouse), the cancer regressed. In the animal (nude mouse) receiving the artificial lymph node transplanted, interferon γ-producing T cells appeared even in the spleen and the like, demonstrating that the T cells in the whole body are activated by transplanting the artificial lymph node.

Bearing in mind that the ratio of interferon γ-producing T cells in innate lymph nodes is about several percent, and in view of a document (JP-A-2004-255110) stating that the ratio of CD4T cells and CD8T cells in conventional artificial lymph nodes is very close to the ratio of CD4T cells and CD8T cells in the T cell region of normal lymph nodes, the ratio of "about 75%" confirmed in the Example is unexpectedly high; it is seen that use of the artificial lymph node constructed in the present invention is excellent as a means for inducing interferon γ-producing T cells. The artificial lymph node of the present invention preferentially produces cancer antigen-specific CD8T cells (also referred to as killer T cells or cytotoxic T cells) compared with innate lymph nodes when stimulated with the cancer antigen used as the immunogen during the production thereof. As a result, in subjects suspected of having cancer cells that express the same cancer antigen, the artificial lymph node of the present invention is expected to have a potent antitumor effect.

(Cancer Therapeutic Agent)

Because the cancer antigen-specific artificial lymph node of the present invention is capable of cancer antigen-specifically producing interferon γ quickly and in large amounts, it can be used as a cancer therapeutic agent in the prophylaxis, treatment, recurrence prevention, and metastasis suppression for blood cancers, including leukemia, and various solid cancers. The present invention provides cancer therapeutic agents comprising the artificial lymph node. The objects of the therapeutic agent of the present invention include not only treatment, but also prophylaxis, recurrence prevention, metastasis suppression and the like.

The amount (size) of the specific antibody-producing artificial lymph node of the present invention to be transplanted to the subject can be set as appropriate according to the recipient. For example, in the case of transplantation to an adult, the artificial lymph node of the present invention may be as large as the intrinsic lymph node, or may be smaller than the intrinsic lymph node but permit transplantation of a plurality of units, and the like. As the site of transplantation, subcutaneous sites, intradermal sites, intratumoral sites, sites under the renal capsule, intramuscular sites, sites in lymph tissue and the like can be mentioned, and because of the low invasiveness and the ease of transplantation surgical technique, subcutaneous transplantation is desirable.

When the subject carries a cancer, it is preferable, from the viewpoint of the therapeutic effect on the cancer, that the therapeutic agent of the present invention be transplanted apart from the onset site of the cancer at an adequate distance.

The cancer antigen-specific artificial lymph node of the present invention also has the following basic structures of lymph nodes that are seemingly essential as the sites of onset of cancer antigen-specific immune responses.

[1] Has a T cell region and a B cell region which are clearly distinguishable.

In the specific antibody-producing artificial lymph node of the present invention, as in normal lymph tissue, the regions of T cells and B cells are discrete, and are referred to as “T cell region” and “B cell region”, respectively. Particularly, a group of B cells is also called “a follicle”.

[2] Dendritic cells that play an important role in immune responses along with T cells and B cells are present.

[3] A B cell region comprising a network of follicular dendritic cells is present in the center.

A follicular dendritic cell (FDC) means “a special cell having a tree-shaped projection that is present in the center of the follicle”, forming a network in the center of the follicle (referred to as FDC network). FDC is a different kind of cell from a dendritic cell.

[4] B cells that are highly positive for germinal center B cell-like PNA (peanut agglutinin) are present.

Prior to antibody production by antigen stimulation, B cells exhibit vigorous growth and differentiation into plasma cells (antibody-producing cells) in the center of the follicle. This site is called the germinal center (GC), and B cells that grow vigorously in this germinal center are referred to as germinal center B cells. Germinal center B cells are known to be highly positive for PNA ($PNA^{high+}$) when stained with PNA because they bind well to PNA.

[5] A HEV-like vasculature that serves as the entrance for lymphocytes in lymph nodes is present.

The high endothelial venula (HEV) is a special vasculature found specifically in secondary lymph tissues such as lymph nodes and Peyer’s patches, and, unlike ordinary blood vessels, has tall (thick-walled) endothelial cells. As such, HEV is expressing a certain adhesion factor and chemokine, serving as the entrance for lymphocytes migrating from bloodstream to these secondary lymph tissues.

(Kit)

The present invention also provides a kit for producing a cancer antigen-specific artificial lymph node. This kit comprises a cancer antigen, an adjuvant capable of inducing cellular immunity, a cytokine expression vector and stromal cells or stromal cells incorporating a cytokine expression vector, dendritic cells and a polymeric biomaterial, which are necessary for producing the cancer antigen-specific artificial lymph node of the present invention in an animal. The dendritic cells contained in this kit are preferably myeloid cell-derived dendritic cells, more preferably activated dendritic cells pulsated with the above-described cancer antigen.

In one embodiment of the present invention, the cancer antigen-specific artificial lymph node of the present invention can be produced directly in the body of the animal to be treated. The present invention also provides such a method of production (also referred to as the direct method of production). The direct method of production comprises the following steps.

(a1) A step for immunizing an animal using a cancer antigen and an adjuvant capable of inducing cellular immunity; and (b1) a step for transplanting an artificial lymph node material consisting of a polymeric biomaterial comprising cytokine-producing stromal cells and dendritic cells to the immunized animal.

The immunization step (a1) in the direct method of production is a step, within the aforementioned immunization step (a), in which immunization is established by stimulation with a cancer antigen molecule circulating in the blood of a cancer-bearing organism. Therefore, the immunization step (a1) is preferably performed by cancer cells born in the body of an animal (preferably a human).

The transplantation step (b1) in the direct method of production is the same as the aforementioned transplantation step (b).

In the direct method of production, for the treatment of a cancer in an immunized animal (preferably a human), the cancer tissue configured with cancer cells born thereby is preferably surgically resected. Therefore, the transplantation step (b1) is preferably performed before, during, or after surgery for the cancer. The transplantation site is preferably apart from the onset site of the cancer at an adequate distance. After a predetermined time has elapsed after transplantation, an artificial lymph node is formed at the transplantation site of the animal (preferably human) to be treated. Thereby, recurrences or metastasis due to cancer cells remaining unresected in the body are significantly suppressed.

EXAMPLES

The present invention is hereinafter described in more detail by means of the following examples, which, however, are for illustrative purposes only and never limit the scope of the invention.

The culture medium, reagents and instruments used in the following production examples and working examples are shown below.

RPMI-1640: GIBCO company

2-Mercaptoethanol: Sigma company

FCS (fetal calf serum): Cell Culture Technologies company

Cell culture medium: RPMI-1640 supplemented with 10% inactivated FCS and 50 μM 2-mercaptoethanol Trypsin-EDTA solution: GIBCO company G418 (geneticin): GIBCO company Recombinant mice GM-CSF (granulocyte-macrophage colony stimulating factor): PeproTech company LPS (lipopolysaccharide): Sigma company Freund’s complete adjuvant: Produced by DIFCO Laboratories company (Michigan USA)

BSA (bovine serum albumin): Sigma company

Culture dishes, culture plates, and Petri dishes; all produced by FALCON company Production Example 1

Preparation of Recombinant Stromal Cells

As stromal cells, TEL-2 cells (Nakashima M. et al., Eur J Immunol. 1990 January; 20(1): 47-53) established from the thymus of a 2-week-old BALB/c mouse were cultured in an RPMI1640 supplemented with 10% fetal calf serum and 50 μM 2-mercaptoethanol. Mouse lymphotoxin α (LTα) or chemokine (CCL21, CCL19 and CXCL13) cDNA was cloned from mouse spleen RNA by RT-PCR (reverse transcription-polymerase chain reaction). Each cDNA was inserted to the EcoRI site of the pCXN2 vector (Niwa H, et al., Gene. 1991 Dec. 15; 108(2): 193-9). This vector comprises a chicken β actin promoter, a CMV enhancer, and a rabbit β globin splicing donor. The expression vector obtained was introduced into TEL-2 cells, and a stable transfectant cell line was obtained after 2 weeks of G418 selection (500 μg/ml). After establishment of the stable transfectant cell line, all cell lines were cultured in a culture medium comprising 200 μg/ml G418. The expression of the introduced gene was confirmed by fluorescence-activated cell sorter (FACS) analysis for LTα, and by chemotaxis assay for chemokines.

Production Example 2

Preparation of Collagen Sponge with Stromal Cells Adhered Thereto

Collagen sponge ("Collagen Sponge" #CS-35, KOKEN, Tokyo, Japan) was cut into small pieces with a given shape and size, and each piece was placed in a well of a 48-well plate. The cytokine-producing TEL-2 stromal cells established according to Production Example 1 were harvested using a Trypsin-EDTA solution, once washed with the culture medium, and suspended in the culture medium, and further once washed with each of PBS (phosphate buffered saline) and 0.1% BSA/PBS, after which 1 ml of 1% BSA/PBS was added to prepare a cell suspension. This cell suspension was centrifuged to precipitate the cells into a pellet form, and the cells were suspended in a small amount of 1% BSA/PBS to yield a homogeneous cell suspension having a very high cell density. This cell suspension was added drop by drop onto the collagen sponge, and the sponge was rubbed to adhere the cells to the collagen sponge. Since the amount of 1% BSA/PBS solution used to suspend the cells and adhere them to the collagen sponge was small, cautions were exerted not to allow the sponge to dry. This 48-well plate containing the collagen sponge having the cells adhered thereto was kept on ice until transplantation under the renal capsule of a mouse.

Production Example 3

Preparation of Activated Dendritic Cells

The bone marrow cavities of the femur and tibia of each female BALB/cAnNCrj mouse at 7 weeks of age to 12 weeks of age were washed with PBS using a syringe equipped with a 26-gauge injection needle to obtain a myeloid cell liquid. This myeloid cell liquid was filtered through a nylon mesh to remove large cell masses and the like, and the filtrate was prepared with a culture medium to yield a cell suspension having a cell density of $2\times10^5$ cells/ml. Although the cell suspension contained a considerable number of erythroid cells, the erythroid cells were ignored and the cell density was calculated to be $2\times10^5$ cells/ml. This cell suspension was transferred to plastic dishes (Petri dishes) 10 cm in diameter at 7 ml per dish, and recombinant mouse GM-CSF was added to obtain a final concentration of 5 ng/ml. Every 3 days or 4 days, half of the cell supernatant was discarded, and a fresh supply of the culture medium supplemented with 5 ng/ml GM-CSF was added. On day 8 or day 9 of cultivation, suspended cells were harvested, a $2\times10^6$ cells/ml cell suspension was prepared with a fresh supply of the culture medium supplemented with 5 ng/ml GM-CSF, 1 μg/ml LPS (or TNF-α) and, if antigen pulsation was performed, the same antigen as the antigen to be inoculated to the mouse before transplantation of the polymeric biomaterial was added, and the cells were cultured in a cell culture dish for 17 to 20 hours to mature and activate dendritic cells.

Production Example 4

Preparation of Collagen Sponge Having Stromal Cells and Dendritic Cells Adhered Thereto Collagen sponge ("Collagen Sponge" #CS-35, KOKEN, Tokyo, Japan) was cut into small pieces with a given shape and size, and each piece was placed in a well of a 48-well plate. Cytokine-producing TEL-2 stromal cells established as directed in Production Example 1 were harvested using a Trypsin-EDTA solution, once washed with a culture medium, suspended in the culture medium, counted, and placed on ice. Activated dendritic cells prepared as directed in Production Example 3 were twice washed with the culture broth, suspended in the culture broth, counted, and placed on ice. In this operation, when the dendritic cells were activated with LPS, the cells were carefully washed not to allow LPS to remain. Thereafter, each type of cell was once washed with each of PBS (phosphate buffered saline) and 0.1% BSA/PBS, after which 1 ml of 1% BSA/PBS was added to yield a homogenous cell suspension having a nearly constant cell density. These suspensions were mixed in a 1:1 ratio by volume, and centrifuged to precipitate the cells into a pellet form, and a small amount of 1% BSA/PBS was added to yield a homogenous cell suspension having a very high cell density. This cell suspension was added drop by drop onto the collagen sponge, and the sponge was rubbed to adhere the cells to the collagen sponge. Since the amount of 1% BSA/PBS solution used to suspend the cells and adhere them to the collagen sponge was small, cautions were exerted not to allow the sponge to dry. This 48-well plate containing the collagen sponge having the cells adsorbed thereto was kept on ice until the collagen sponge having the cells adhered thereto was transplanted under the renal capsule of the mouse.

Production Example 5

Transplantation of Collagen Sponge to Mice

An antigen dissolved in a buffer solution (PBS) and Freund's complete adjuvant in an equal volume were taken in two glass syringes, respectively, and the two syringes were connected using a double-hub needle. First, the antigen solution in the aqueous layer was injected to Freund's complete adjuvant in the oily layer, and thereafter alternative injections were repeated to form an emulsion of the antigen solution and the adjuvant.

Each female BALB/cAnNCrj mouse at 8 weeks of age to 10 weeks of age (Charles River Japan Inc., reared in a mouse room under SPF conditions) was anesthetized, and 100 μl of the antigen emulsion was subcutaneously injected to the caudal root. For 3 weeks to 4 weeks, the mice was reared, waiting for the development of immunity against the antigen.

Each female BALB/cAnNCrj mouse at 8 weeks of age to 14 weeks of age (Charles River Japan Inc., reared in a mouse room under SPF conditions) was anesthetized, its body surface was disinfected with 70% ethanol, and the animal was brought into a right lateral decubitus position. The skin in the left hypochondrium was incised by about 1 cm, and the muscular layer just thereunder was also incised by nearly the same size. Adipose tissue around the kidneys was pinched with tweezers, and the kidneys were drawn out from the body. While making an examination by stereoscopic microscopy, the renal capsule was opened using sharp-edged tweezers while exerting cautions not to hurt the renal parenchyma, and the collagen sponge prepared in Production Example 4 was inserted between the renal capsule and the kidney. Usually, in order to perform transplantation at two sites in each kidney (near the upper pole and lower pole of kidney), a total of four collagen sponges having stromal cells adhered thereto per mouse were transplanted to each of the left and right kidneys. Three weeks after transplantation, the transplanted tissue (hereinafter referred to as artificial lymph node) was recovered.

Example 1

Analysis of Artificial Lymph Node in Mice in Production Example 5

After the artificial lymph node recovered in Production Example 5 was washed with PBS, it was transplanted to a 6-well plate containing a culture medium, and thoroughly ground using a slide glass. The cell liquid obtained by the grinding was filtered through a nylon mesh to remove large cell masses and the like, and the cell suspension was recovered in a 15 ml centrifugal tube. After the recovered cell suspension was adjusted to $1\times10^6$ cells/ml with a culture medium with 2 μM monensin dissolved therein, it was sown to a 24-well plate coated with an anti-TCR antibody at 1 ml per well. Coating of the 24-well plate with the anti-TCR antibody was performed by adding drop by drop 250 μl of 3 μg/ml of the anti-TCR antibody to each well on the previous day, and incubating the plate at 4° C. overnight. After the sown cells were cultured in a $CO_2$ incubator for 6 hours, the cells were detached by gentle pipetting and recovered in a FACS tube. After the recovered cell liquid was twice washed with PBS, 350 μl of 3% BSA/PBS was added, and the liquid was incubated on ice for 15 minutes. Thereafter, the 3% BSA/PBS was removed via centrifugation, various antibody solutions were added to the cell pellet, and the liquid was again incubated on ice for 45 minutes in order to stain the cell surface antigen. After completion of staining of the cell surface antigen, the cells were twice washed with PBS, after which 350 μl of 4% PFA was added, and the cells were incubated at room temperature for 10 minutes, to thereby achieve formalin fixation. Thereafter, the cells were twice washed with a FACS buffer consisting of 2% FCS/PBS, after which 350 μl of Permealize buffer was added, and the cells were incubated on ice for 10 minutes. After the cells were again twice washed with the FACS buffer, 350 μl of 3% BSA/PBS was added, and the liquid was incubated on ice for 15 minutes. Thereafter, the 3% BSA/PBS was removed via centrifugation, various antibody solutions were added to the cell pellet, and the liquid was again incubated for 45 minutes in order to stain the intracellular antigens such as IFN-γ and IL-4. After completion of intracellular staining, the cells were washed with the FACS buffer and filtered through a nylon mesh to remove the cell masses. The cell liquid after staining thus obtained was analyzed using a FACS calibrator.

Example 2

Transplantation of Artificial Lymph Node to Cancer-Bearing Mice

Cancer cells obtained by cultivation and the like were recovered and washed with PBS, after which they were suspended in PBS at $1\times10^6$ to $10^8$ cells/ml. Each female BALB/c SCID mouse at 8 weeks of age to 10 weeks of age (Charles River Japan Inc., reared in a mouse room under SPF conditions) was anesthetized, and 100 μl of the cancer cell liquid was subcutaneously injected to the back. Then the mouse was reared for 6 days, waiting for tumor mass formation. The cancer-bearing mouse wherein the tumor mass had been formed was anesthetized, its body surface was disinfected with 70% ethanol, and the animal was brought into a right lateral decubitus position. The skin of the left costal area was incised by about 1 cm, and the muscular layer just thereunder was also incised by nearly the same size. Adipose tissue around the kidneys were pinched with tweezers, and the kidneys were drawn out from the body. While making an examination by stereoscopic microscopy, the renal capsule was opened using sharp-edged tweezers while exerting cautions not to hurt the renal parenchyma, and the artificial lymph node recovered in Production Example 5 was inserted between the renal capsule and the kidney. Usually, in order to perform transplantation at two sites in each kidney (near the upper pole and lower pole of kidney), a total of four artificial lymph nodes per mouse were transplanted to the left and right kidneys.

The results of Example 1 are shown in FIGS. 2A and 2B. FIG. 2A shows interferon γ production in the artificial lymph node. From FIG. 2B, it is suggested that the interferon γ-producing cells may be CD8-positive cells, CD4-positive cells and NK cells. The results of Example 2 are shown in FIGS. 2C and 2D. From FIG. 2C, it is seen that in the cancer-bearing mouse, CD8-positive killer cells derived from the artificial lymph node grow even in the spleen and produce interferon γ. Meanwhile, from FIG. 2D, it is seen that in the cancer-bearing mouse not receiving the artificial lymph node transplanted, interferon γ is not produced.

The results of Example 2 are shown in FIG. 3. From FIG. 3, it is seen that in the cancer-bearing mice receiving the artificial lymph node transplanted, the cancer tissue regressed dramatically after elapse of 30 days after transplantation, whereas in the cancer-bearing mice without transplantation, no cancer regression was observed.

Production Example 6

Mouse Immunization by Cancer Cell Transplantation and Transplantation of Collagen Sponge to Mice Each female BALB/cAnNCrj mice at 8 weeks of age to 10 weeks of age (Charles River Japan Inc., reared in a mouse room under SPF conditions) was anesthetized, and $5\times10^6$ cells of the B lymphoma cell line A20-OVA (Balb/c mouse-derived cancer cells expressing ovalbumin antigen on the cell surface thereof, supplied by Professor Nishimura at Hokkaido University) were intradermally transplanted to the caudal root. Six to 14 days after transplantation, the cancer mass that had grown from the recipient mouse was surgically resected as carefully as possible.

Figure 4:
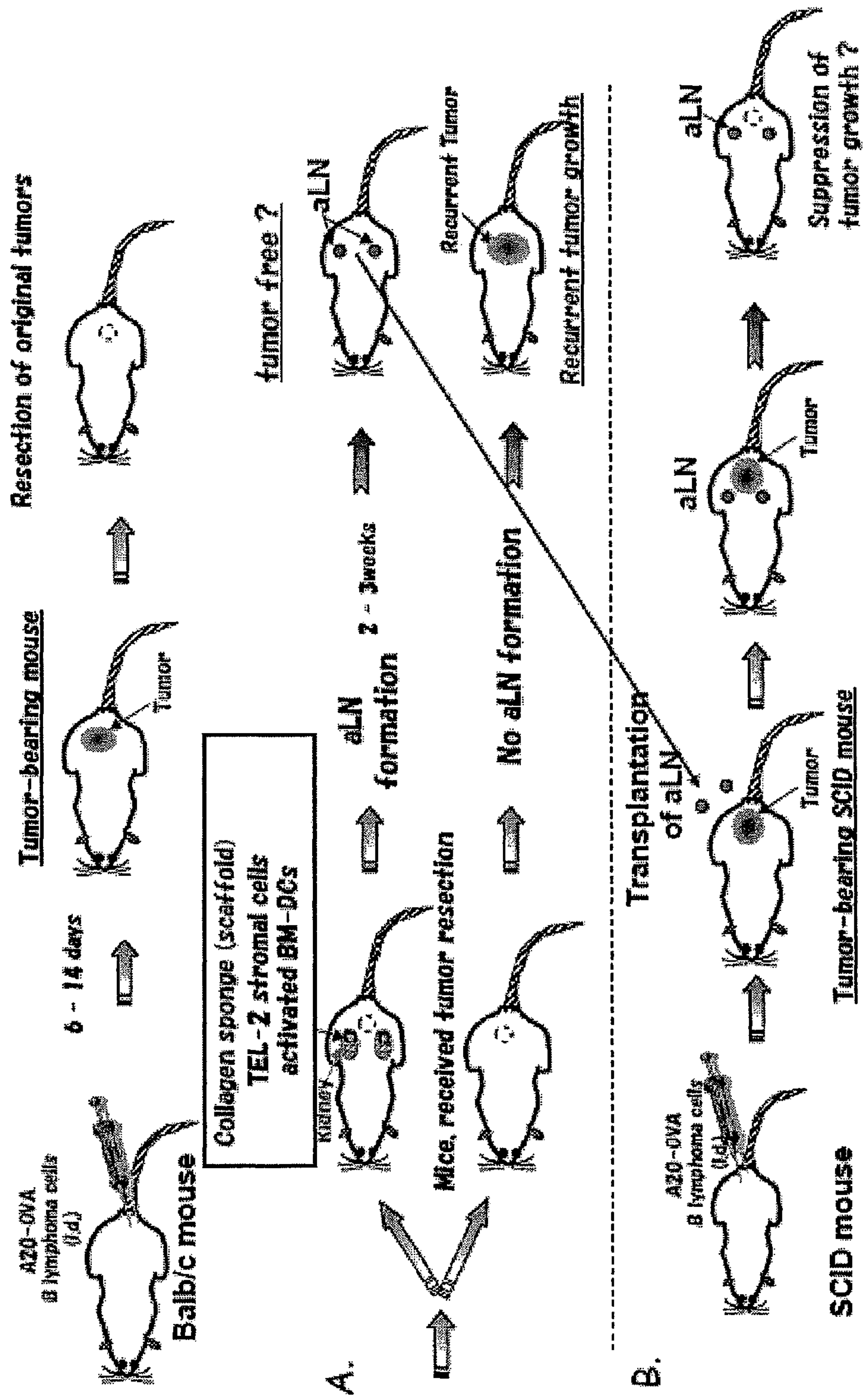
FIG. 4 shows a schematic diagram of artificial lymph node formation in a cancer-bearing animal.

During resection of the cancer, the skin in the left hypochondrium was incised by about 1 cm, and the muscular layer just thereunder was also incised by nearly the same size. Adipose tissue around the kidneys was pinched with tweezers, and the kidneys were drawn out from the body. While making an examination by stereoscopic microscopy, the renal capsule was opened using sharp-edged tweezers while exerting cautions not to hurt the renal parenchyma, and the collagen sponge prepared in Production Example 4 was inserted between the renal capsule and the kidney. In order to perform transplantation at two sites in each kidney (near the upper pole and lower pole of kidney), a total of four collagen sponges with stromal cells attached thereto per mouse were transplanted to each of the left and right kidneys. An outline of the steps in this Production Example is shown in FIG. 4A.

In the group of mice with transplantation, artificial lymph node formation was confirmed 2 weeks after collagen sponge transplantation. For control, a group of mice undergoing cancer resection only were also reared. In these mouse groups, the presence or absence of cancer recurrences was examined until 3 weeks after cancer cell transplantation. The results are shown in FIG. 5.

The artificial lymph node formed in this Production Example was proved to potently suppress cancer recurrences in the mice wherein the artificial lymph node had been formed. Almost no metastasis was observed in the associated lymph nodes. Meanwhile, in the mouse group not receiving the artificial lymph node material transplanted, despite the normal immune potential, the cancer expanded rapidly, and lymph node metastasis occurred remarkably. This is probably because a small number of cancer cells remaining after cancer resection migrated to the artificial lymph node and strongly induced antitumor immune responses. In fact, it was confirmed that interferon γ-producing T cells had increased in large amounts in the aforementioned artificial lymph node. From this fact, it seems that even in human cancer patients, cancer recurrences or metastasis can be effectively suppressed by transplanting an appropriate artificial lymph node material that is compatible with the human during surgical resection of the cancer, and constructing an artificial lymph node in the body.

Example 3

Transplantation of Artificial Lymph Node of Production Example 6 to Cancer-Bearing Mice The artificial lymph nodes formed in the mice after cancer resection in Production Example 6 were recovered, and they were transplanted under the renal capsule of a cancer-bearing SCID mouse having cells of the B lymphoma cell line A20-OVA transplanted thereto in advance, in the same manner as Example 2. An outline of the steps of this Example is shown in FIG. 4B. For control, cancer-bearing SCID mice not receiving the artificial lymph node transplanted were also reared. A comparison of the degree of progression of cancer was made between the group of mice with transplantation and the group of mice without transplantation until 3 weeks after transplantation of cancer cells. The results are shown in FIG. 5.

As a result, it was found that in the cancer-bearing mice receiving the artificial lymph node transplanted, cancer growth was strongly suppressed, whereas in the cancer-bearing mice without transplantation, cancer progression was remarkable. Therefore, the artificial lymph node of the present invention seems to be capable of effectively suppressing cancer progression even in surgically unresectable cancers.

INDUSTRIAL APPLICABILITY

According to the present invention, an artificial lymph node useful in cancer treatment is provided to thereby contribute to the development of a novel therapeutic method for cancer.

This application is based on a patent application No. 2006-331114 filed in Japan (filing date: Dec. 7, 2006), the contents of which are incorporated in full herein by this reference.

The invention claimed is:

1. A method of producing an artificial lymph node comprising the following steps:

(a) a step for immunizing a non-human animal using a cancer antigen and at least one adjuvant selected from the group consisting of Freund's complete adjuvant, CpG adjuvant, liposome, BCG, polyI:C, R848, and lipopolysaccharide; and (b) a step for transplanting an artificial lymph node material consisting of a polymeric biomaterial comprising cytokine-producing stromal cells and dendritic cells to the immunized non-human animal, thereby producing an artificial lymph node that induces cancer antigen-specific immune responses and enriches IFN-γ producing CD8-positive killer T cells or NK cells with cancer cytotoxic activity.

2. The method of claim 1, further comprising the following step:

(c) a step for recovering the artificial lymph node constructed in the foregoing transplantation step from the recipient non-human animal.

3. The method of claim 1, wherein the dendritic cells are myeloid cell-derived dendritic cells.

4. The method of claim 1, wherein the polymeric biomaterial is collagen sponge.

5. The method of claim 1, wherein the cytokine is a lymphotoxin and/or a chemokine.

6. The method of claim 1, wherein the non-human animal is a non-human mammal.

7. An artificial lymph node obtained by the method of claim 1, wherein the artificial lymph node induces cancer antigen-specific immune responses and enriches IFN-γ producing CD8-positive killer T cells or NK cells with cancer cytotoxic activity.

8. An artificial lymph node obtained by the method of claim 2, wherein the artificial lymph node induces cancer antigen-specific immune responses and enriches IFN-γ producing CD8-positive killer T cells or NK cells with cancer cytotoxic activity.

9. The artificial lymph node of claim 7, which comprises cancer antigen-specific interferon γ-producing cells when stimulated with the cancer antigen.

10. The artificial lymph node of claim 8, which comprises cancer antigen-specific interferon γ-producing cells when stimulated with the cancer antigen.

11. A cancer therapeutic agent comprising the artificial lymph node of claim 7.

12. A cancer therapeutic agent comprising the artificial lymph node of claim 8.

13. A kit for producing an artificial lymph node for cancer treatment, comprising the following:

(a) a cancer antigen;

(b) at least one adjuvant selected from the group consisting of Freund's complete adjuvant, CpG adjuvant, liposome, BCG, polyI:C, R848, and lipopolysaccharide;

(c) a cytokine expression vector and stromal cells, or stromal cells incorporating a cytokine expression vector;

(d) dendritic cells; and (e) a polymeric biomaterial, wherein the artificial lymph node induces cancer antigen-specific immune responses and enriches IFN-γ producing CD8-positive killer T cells or NK cells with cancer cytotoxic activity.

14. The kit of claim 13, wherein the dendritic cells are myeloid cell-derived dendritic cells.

15. The kit of claim 13, wherein the polymeric biomaterial is collagen sponge.

16. The kit of claim 13, wherein the cytokine is a lymphotoxin and/or a chemokine.

17. A method of producing an artificial lymph node comprising the following steps:

(a1) a step for immunizing an animal using a cancer antigen and at least one adjuvant selected from the group consisting of Freund's complete adjuvant, CpG adjuvant, liposome, BCG, polyI:C, R848, and lipopolysaccharide, wherein the immunization step is performed with cancer cells born in the body of the animal; and (b1) a step for transplanting an artificial lymph node material consisting of a polymeric biomaterial comprising cytokine-producing stromal cells and dendritic cells to the immunized animal, thereby producing an artificial lymph node that induces cancer antigen-specific immune responses and enriches for IFN-γ producing CD8-positive killer T cells or NK cells with cancer cytotoxic activity.

18. The method of claim 17, wherein the animal is a human.

19. A method of producing an artificial lymph node comprising the following steps:

(a1) a step for immunizing an animal using a cancer antigen and at least one adjuvant selected from the group consisting of Freund's complete liposome, BCG, polyI:C, R848, and lipopolysaccharide; and (b1) a step for transplanting an artificial lymph node material consisting of a polymeric biomaterial comprising cytokine-producing stromal cells and dendritic cells to the immunized animal, wherein the transplantation step is performed before, during, or after surgery for a cancer in the animal, thereby producing an artificial lymph node that induces cancer antigen-specific immune responses and enriches for IFN-γ producing CD8-positive killer T cells or NK cells with cancer cytotoxic activity.

20. An antigen-specific therapeutic method for a cancer, comprising steps:

(a1) a step for immunizing an animal using a cancer antigen and at least one adjuvant selected from the group consisting of Freund's complete adjuvant, CpG adjuvant, liposome, BCG, polyI:C, R848, and lipopolysaccharide, wherein the immunization step is performed with cancer cells born in the body of the animal; and (b1) a step for transplanting an artificial lymph node material consisting of a polymeric biomaterial comprising cytokine-producing stromal cells and dendritic cells to the immunized animal to produce an artificial lymph node, wherein the artificial lymph node induces cancer antigen-specific immune responses and enriches for IFN-γ producing CD8-positive killer T cells or NK cells having cancer cytotoxic activity.

21. The therapeutic method of claim 20, wherein the animal is a human.

* * * * *

UNITED STATES PATENT AND TRADEMARK OFFICE

CERTIFICATE OF CORRECTION

PATENT NO. : 8,101,195 B2
APPLICATION NO. : 11/939885
DATED : January 24, 2012
INVENTOR(S) : Watanabe et al.

It is certified that error appears in the above-identified patent and that said Letters Patent is hereby corrected as shown below:

Claim 19, column 20, line 5:

"Freund's complete liposome" should read "Freund's complete adjuvant, CpG adjuvant, liposome"

Signed and Sealed this
Fourth Day of September, 2012

David J. Kappos
*Director of the United States Patent and Trademark Office*